(12) United States Patent
Gerber et al.

(10) Patent No.: US 7,766,862 B2
(45) Date of Patent: Aug. 3, 2010

(54) BASELINE ACQUISITION FOR INFECTION MONITORING

(75) Inventors: Martin T. Gerber, Maple Grove, MN (US); John C. Rondoni, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 75 days.

(21) Appl. No.: 12/023,073

(22) Filed: Jan. 31, 2008

(65) Prior Publication Data

US 2008/0262380 A1   Oct. 23, 2008

Related U.S. Application Data

(63) Continuation-in-part of application No. 11/737,173, filed on Apr. 19, 2007, now abandoned, and a continuation-in-part of application No. 11/737,170, filed on Apr. 19, 2007, and a continuation-in-part of application No. 11/737,176, filed on Apr. 19, 2007, now Pat. No. 7,682,355, and a continuation-in-part of application No. 11/737,169, filed on Apr. 19, 2007, now abandoned, and a continuation-in-part of application No. 11/737,171, filed on Apr. 19, 2007, now abandoned, and a continuation-in-part of application No. 11/737,181, filed on Apr. 19, 2007, now Pat. No. 7,604,629, and a continuation-in-part of application No. 11/737,179, filed on Apr. 19, 2007, and a continuation-in-part of application No. 11/737,180, filed on Apr. 19, 2007, now Pat. No. 7,611,483.

(51) Int. Cl.
*A61M 31/00* (2006.01)

(52) U.S. Cl. .......................... 604/66; 600/549

(58) Field of Classification Search .............. 604/890.1, 604/891.1, 65, 66–67; 600/549
See application file for complete search history.

(56) References Cited

U.S. PATENT DOCUMENTS

| 5,029,582 | A | 7/1991 | Lekholm |
| 5,181,905 | A | 1/1993 | Flam |
| 5,546,955 | A | 8/1996 | Wilk |
| 5,807,270 | A | 9/1998 | Williams |
| 5,820,263 | A | 10/1998 | Ciobanu |

(Continued)

FOREIGN PATENT DOCUMENTS

DE    10150343    4/2003

(Continued)

OTHER PUBLICATIONS

U.S. Appl. No. 11/737,180, filed Apr. 19, 2007, Gerber.

(Continued)

*Primary Examiner*—Kevin C Sirmons
*Assistant Examiner*—Deanna K Hall
(74) *Attorney, Agent, or Firm*—Campbell Nelson Whipps LLC

(57) ABSTRACT

A method includes obtaining a baseline value for an indicator of infection in proximity to an implantable medical device and monitoring the indicator of infection in proximity to the device. The method further includes determining whether the monitored indicator is indicative of infection in proximity to the device. The determination as to whether the monitored indicator is indicative of infection includes comparing a value associated with the monitored indicator to the baseline value.

13 Claims, 9 Drawing Sheets

U.S. PATENT DOCUMENTS

| | | | |
|---|---|---|---|
| 6,113,539 | A | 9/2000 | Ridenour |
| 6,135,968 | A | 10/2000 | Brounstein |
| 6,248,080 | B1 | 6/2001 | Miesel |
| 6,282,444 | B1 | 8/2001 | Kroll |
| 6,356,774 | B1 | 3/2002 | Bernstein |
| 6,558,351 | B1 | 5/2003 | Steil |
| 6,963,772 | B2 | 11/2005 | Bloom |
| 6,970,741 | B1 | 11/2005 | Whitehurst |
| 7,049,824 | B2 | 5/2006 | Shabino |
| 2002/0042596 | A1 | 4/2002 | Hartlaub |
| 2003/0032892 | A1 | 2/2003 | Erlach |
| 2003/0199783 | A1 | 10/2003 | Bloom |
| 2003/0216677 | A1 | 11/2003 | Pan |
| 2004/0066313 | A1 | 4/2004 | Ong |
| 2005/0012610 | A1 | 1/2005 | Liao |
| 2005/0090761 | A1 | 4/2005 | Carney |
| 2005/0096584 | A1 | 5/2005 | Ferek-Petric |
| 2006/0047218 | A1* | 3/2006 | Bloom et al. ............... 600/547 |
| 2006/0062852 | A1 | 3/2006 | Holmes |
| 2006/0079793 | A1 | 4/2006 | Mann |
| 2006/0149331 | A1 | 7/2006 | Mann |
| 2006/0224088 | A1 | 10/2006 | Roche |
| 2006/0271108 | A1 | 11/2006 | Libbus |

FOREIGN PATENT DOCUMENTS

| | | |
|---|---|---|
| GB | 2 405 203 | 2/2005 |
| WO | WO 02/068049 | 9/2002 |
| WO | WO 2005/000091 | 1/2005 |
| WO | WO 2005/000160 | 1/2005 |
| WO | WO 2006/013585 | 2/2006 |
| WO | WO 2006/048554 | 5/2006 |
| WO | WO 2007/028035 | 3/2007 |

OTHER PUBLICATIONS

Robicsek, F., et al. The value of thermography in the early diagnosis of postoperative sternal wound infections. Thoracic & Cardiovascular Surgeon, 1984. 32(4): p. 260-5.

Saxena, A.K., et al. Thermography of Clostridium perfringens infection in childhood. Pediatric Surgery International, 1999. 15(1): p. 75-6.

U.S. Appl. No. 11/737,176, filed Apr. 19, 2007, Gerber.
U.S. Appl. No. 11/737,181, filed Apr. 19, 2007, Gerber.
U.S. Appl. No. 11/737,179, filed Apr. 19, 2007, Gerber.
U.S. Appl. No. 11/737,171, filed Apr. 19, 2007, Gerber.
U.S. Appl. No. 11/737,170, filed Apr. 19, 2007, Gerber.
U.S. Appl. No. 11/737,169, filed Apr. 19, 2007, Gerber.
U.S. Appl. No. 11/737,173, filed Apr. 19, 2007, Gerber.
U.S. Appl. No. 12/023,076, filed Jan. 31, 2008, Gerber.
Waterman, N.G., L. Goldberg, and T. Appel, Tissue temperatures in localized pyogenic infections, American Journal of Surgery, 1969. 118(1): p. 31-5.

PCT International Search Report dated Oct. 10, 2007.
PCT International Search Report dated Nov. 19, 2007.
PCT International Search Report dated Dec. 5, 2007.

\* cited by examiner

BASELINE ACQUISITION FOR INFECTION MONITORING

RELATED APPLICATIONS

This application is a continuation-in-part of U.S. patent application Ser. No. 11/737,173, filed on Apr. 19, 2007, published on Oct. 23, 2008 as U.S. 2008/0262332; U.S. patent application Ser. No. 11/737,170, filed on Apr. 19, 2007, published on Oct. 23, 2008 as U.S. 2008/0262331; U.S. patent application Ser. No. 11/737,176, filed on Apr. 19, 2007, now U.S. Pat. No. 7,682,355; U.S. patent application Ser. No. 11/737,169, filed on Apr. 19, 2007, published on Oct. 23, 2008 as U.S. 2008/0262374; U.S. patent application Ser. No. 11/737,171, filed on Apr. 19, 2007, published on Oct. 23, 2008 as U.S. 2008/0262378; U.S. patent application Ser. No. 11/737,181, filed on Apr. 19, 2007, now U.S. Pat. No. 7,604,629; U.S. patent application Ser. No. 11/737,179, filed on Apr. 19, 2007, published on Jan. 1, 2009 as U.S. 2009/0005770; and U.S. patent application Ser. No. 11/737,180, filed on Apr. 19, 2007, now U.S. Pat. No. 7,611,483, each of which applications are hereby incorporated herein by reference in their respective entireties to the extent they do not conflict with the disclosure presented herein.

FIELD

This disclosure relates, inter alia, to implantable medical devices. More particularly, it relates to systems, devices and methods for monitoring infection in proximity to medical devices implanted in patients and for acquiring a baseline for determining whether the indicator is indicative of infection.

BACKGROUND

Infection associated with implantation of medical devices is a serious health and economic concern. Today, infections associated with implanted medical devices are not very common due to care and precautions taken during surgical implantation of the devices. However, when infection associated with an implanted medical device (IMD) does occur, explanting the device is often the only appropriate course of action.

For IMDs having a battery powered component, such as implantable cardiac pacemakers, cardioverter/defibrillators having pacing capabilities, other electrical stimulators including spinal cord, deep brain, nerve, and muscle stimulators, infusion devices, cardiac and other physiologic monitors, cochlear implants, etc., the battery powered component is typically enclosed in a housing that is implanted subcutaneously at a surgically prepared site, referred to as a "pocket". Associated devices, such as elongated medical electrical leads or drug delivery catheters, extend from the pocket to other subcutaneous sites or deeper into the body to organs or other implantation sites.

Surgical preparation and implantation are conducted in a sterile field, and the IMD components are packaged in sterile containers or sterilized prior to introduction into the sterile field. However, despite these precautions, there always is a risk of introduction of microbes into the pocket. Surgeons therefore typically apply disinfectant or antiseptic agents to the skin at the surgical site prior to surgery, directly to the site before the incision is closed, and prescribe oral antibiotics for the patient to ingest during recovery.

Despite these precautions, infections do occur. In addition, once the pocket becomes infected, the infection can migrate along the lead or catheter to the heart, brain, spinal canal or other location in which the lead or catheter is implanted. Such a migrating infection can become intractable and life-threatening, requiring removal of the IMD in the pocket and associated devices, such as leads and catheters. Removal of a chronically implanted lead or catheter can be difficult and dangerous. Accordingly, aggressive systemic drug treatment is prescribed to treat such infections. However, early detection of infection associated with implanted medical devices may allow for earlier intervention, resulting in fewer device explants.

Monitoring of infection through the use of sensors, such as temperature and pH sensors that can provide information indicative of infection has been proposed. However, various factors may affect the reliability and accuracy of such indicators and determinations as to whether an infection is present in proximity to the implanted device based on such indicators. For example, a sensor may respond differently to a similar stimulus at different times (e.g., sensor drift or degradation), the location of a patient in which the device is implanted may affect a value associated with a sensed indicator, and patient-to-patient variability regarding such indicators may affect whether an accurate determination of whether an indicator is indicative of infection. Suitable methods, systems and devices to account for such various factors have not been proposed.

SUMMARY

The present disclosure describes, inter alia, systems, devices and methods that can be used to monitor an infection in proximity to an implanted medical device, where a determination as to whether the monitored indicator is indicative of infection includes comparing a value associated with the monitored indicator to a baseline value. The baseline value may be obtained at appropriate times to improve accuracy of the determination as to whether the monitored indicator is indicative of infection. For example, the baseline may be obtained at times close to when a determination regarding infection is made or at times when the implanted system or the patient is determined to be stable.

In an embodiment, a method described herein includes obtaining a baseline value for an indicator of infection in proximity to an implantable medical device. The method further includes monitoring the indicator of infection in proximity to the device and determining whether the monitored indicator is indicative of infection in proximity to the device. The determination includes comparing a value associated with the monitored indicator to the baseline value.

By providing devices, systems and methods that obtain baseline values more accurate determinations as whether a monitored indicator is indicative of infection may be made. Other advantages will be readily understood from the following detailed descriptions when read in conjunction with the accompanying drawings.

The drawings are not necessarily to scale. Like numbers used in the figures refer to like components, steps and the like. However, it will be understood that the use of a number to refer to a component in a given figure is not intended to limit the component in another figure labeled with the same number.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present invention. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

The present disclosure describes, inter alia, systems, devices and methods that may be used to monitor an infection in proximity to an implanted medical device. The systems, devices and methods determine whether the monitored indicator is indicative of infection. The determination includes comparing a value associated with the monitored indicator to a baseline value. The baseline value may be obtained at appropriate times to improve accuracy of the determination as to whether the monitored indicator is indicative of infection. For example, the baseline may be obtained at times close to when a determination regarding infection is made, at times when the implanted system or the patient is determined to be stable, or at times deemed appropriate by the patient or a healthcare provider.

Any implantable medical device or system for which it is desirable to monitor infection may be modified according to the teachings provided herein. For example, it may be desirable to monitor infection in association with implantation of a monitoring device, such as for monitoring brain activity, cardiac activity, blood pressure, glucose levels, patient movement, and the like, or a therapy delivering device, such as infusion devices or implantable electrical signal generators, including cardiac defibrillators, pacemakers, neurostimulators, gastric stimulators, cochlear implants, and the like.

Figure 1:
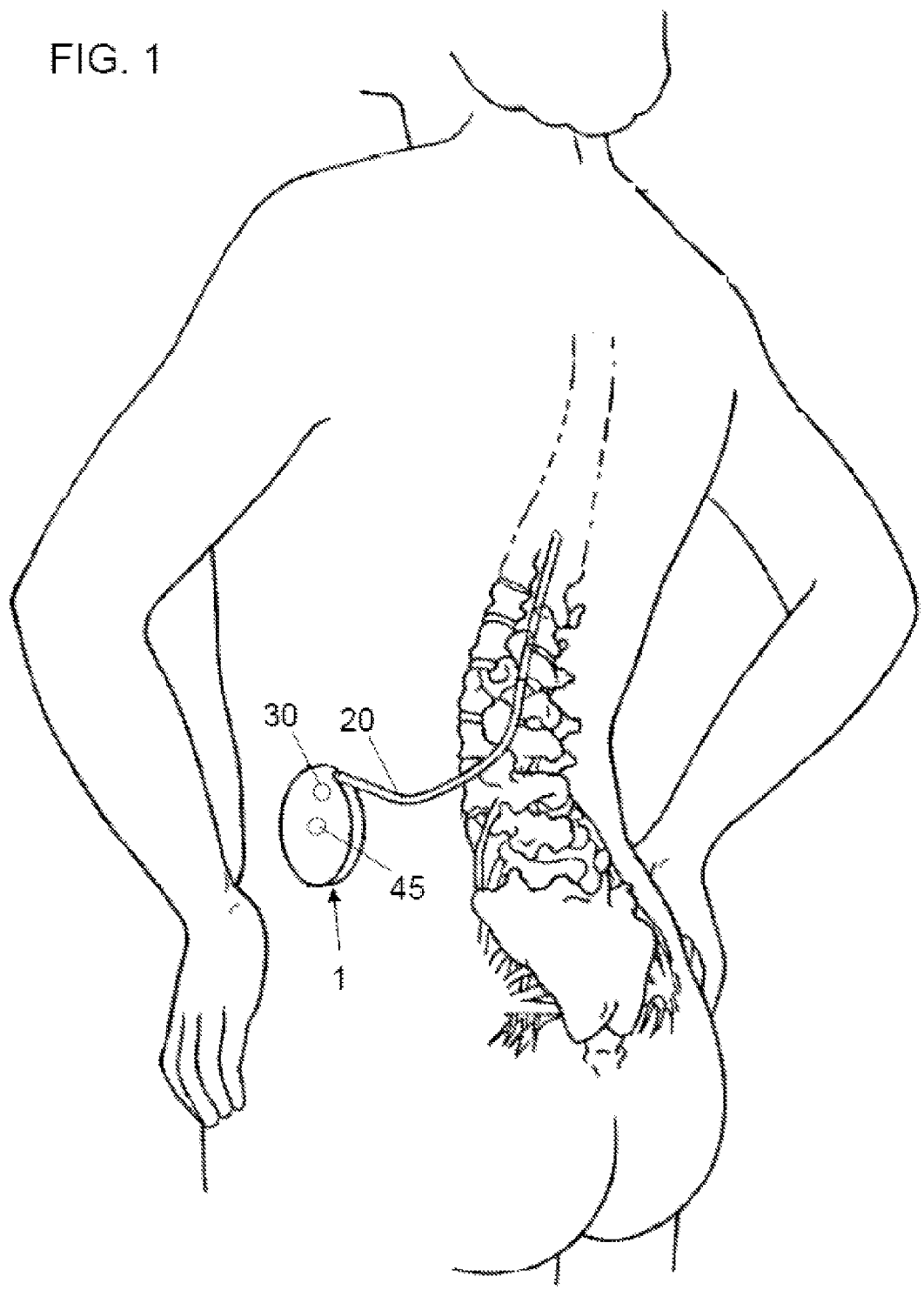
FIG. 1 is a diagrammatic representation of a perspective view of an environment of an infusion system implanted in a patient.
Figure 2:
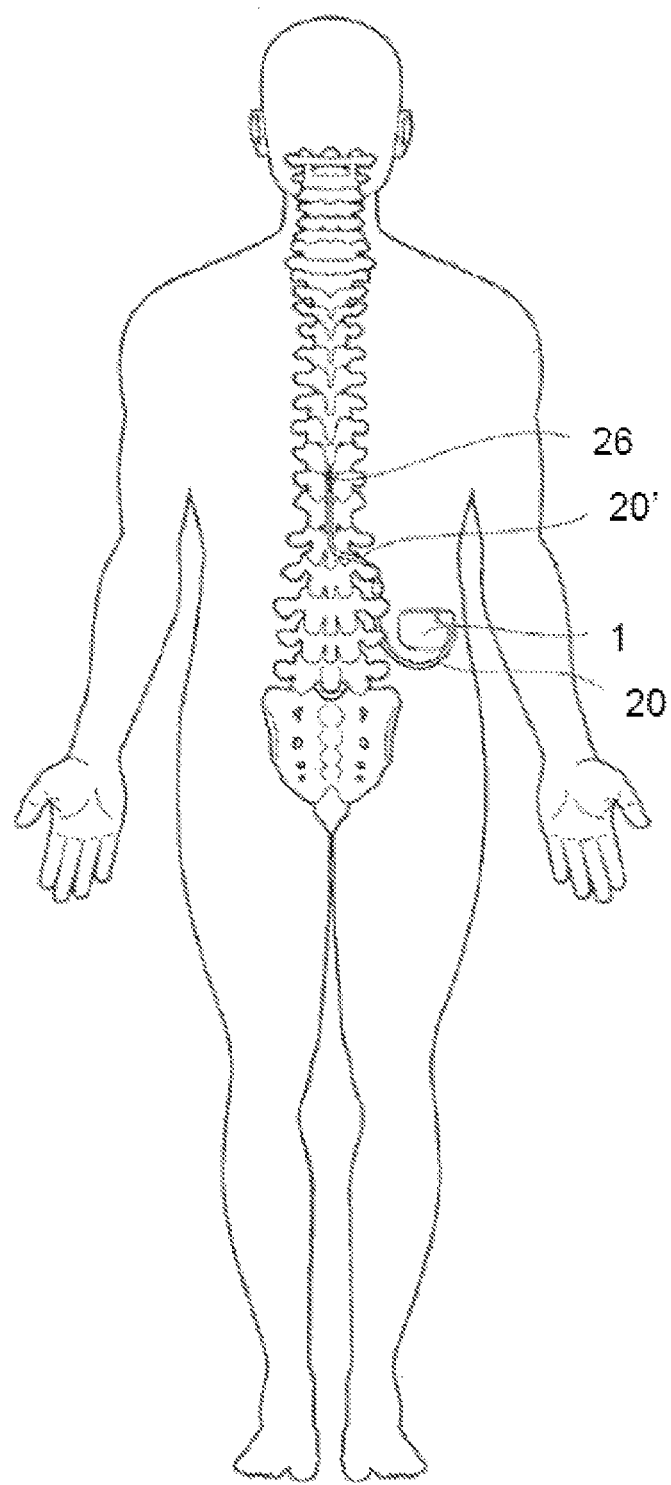
FIG. 2 is a diagrammatic representation of a perspective view of an environment of an electrical signal generator system implanted in a patient
Figure 3A:
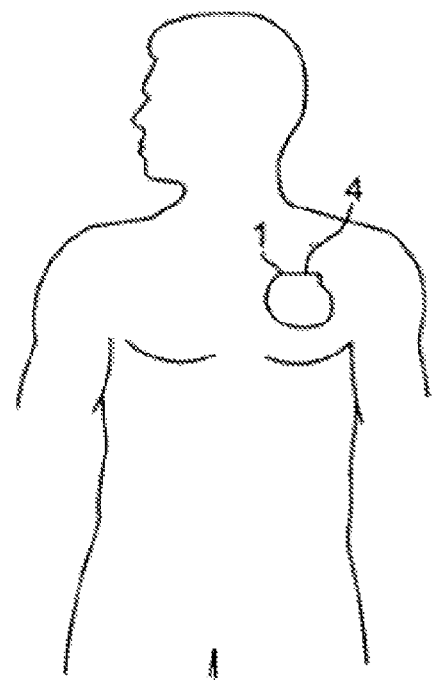
FIGS. 3A-D are a diagrammatic representations of a perspective views of environments of medical devices implanted in patients.
Figure 3B:
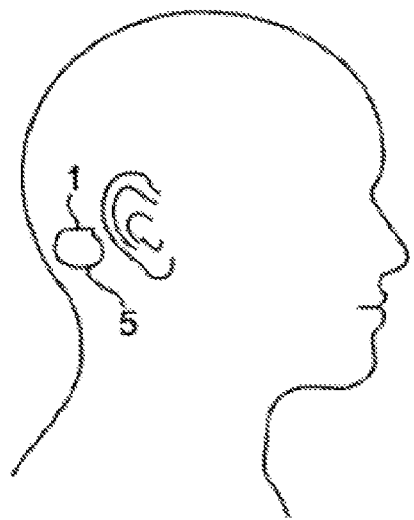
Figure 3C:
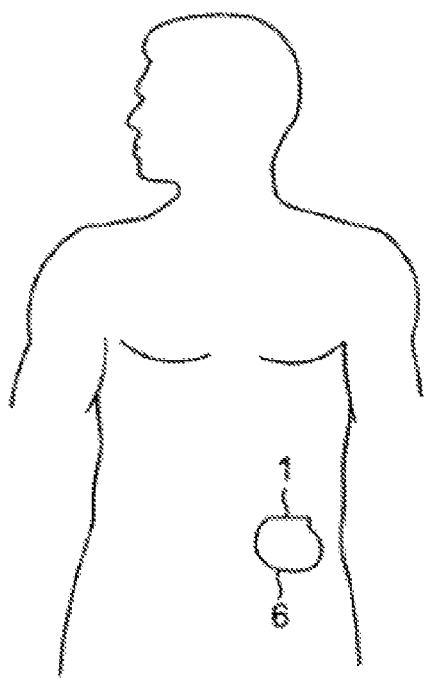
Figure 3D:
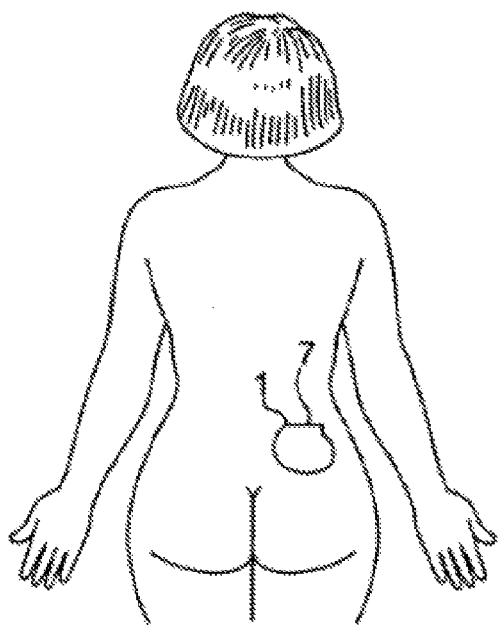

Referring to FIGS. 1 and 2, general illustrative environments for implanted active therapy delivering medical devices 1 and associated devices 20 are shown. In the depicted embodiments, active medical device 1 is subcutaneously implanted in an abdominal region of a patient. A distal portion of associated device 20 is intrathecally inserted into the patient's spinal canal through a lumbar puncture and advanced rostrally to a desired location (FIG. 1) or epidurally placed along a suitable location of spinal cord (FIG. 2). Proximal end of associated device 20 is tunneled subcutaneously to location of active device 1, where it may be connected to active device 1. While distal portion of associated device 20 is shown in FIGS. 1 and 2 as being located in or on spinal cord, it will be understood that associated device 20 may be placed at any location in patient for which it is desirable to administer therapy generated or delivered by active medical device 1.

In the embodiment shown in FIG. 1, active implantable device 1 is an infusion device, and associated device 20 is a catheter. Catheter 20 is typically a flexible tube with a lumen running from the proximal end of catheter 20 to one or more delivery regions that are typically located at the distal portion of catheter 20. Proximal portion of catheter 20 is connected to infusion device 20. Distal portion of catheter 20 is positioned at a target location in the patient to deliver fluid containing therapeutic agent from infusion device 1 to patient through a delivery region of catheter 20. Infusion device 1, such as Medtronic Inc.'s SynchroMed™ II implantable programmable pump system, includes a reservoir (not shown) for housing a therapeutic substance and a refill port 45 in fluid communication with reservoir. The reservoir may be refilled by percutaneously inserting a needle (not shown) into patient such that needle enters refill port 45, and fluid containing therapeutic substance may be delivered into reservoir from needle via refill port 45. Infusion device 1 shown in FIG. 1 also includes a catheter access port 30 that is in fluid communication with the catheter 20. Fluid may be injected into or withdrawn from patient through catheter 20 via catheter access port 30 by percutaneously inserting a needle into access port 30. Each entry of needle across patient's skin to gain access refill port 45 or access port 30 results in the possibility of infection in proximity to the active medical device 1.

In the embodiment shown in FIG. 2, active implantable device 1 is an electrical signal generator, such as Medtronic Inc.'s Restore™ Advanced implantable neurostimulator, and associated devices 20, 20' are a lead extension 20 and lead 20'. Lead 20' includes one or more electrical contacts (not shown) on its proximal end portion and one or more electrodes on its distal end portion 26. The contacts and electrodes are electrically coupled via wires running through lead 20'. Electrical signals generated by the signal generator 1 may be delivered to lead 20 through the contacts and then to the patient through the electrodes. As shown in FIG. 2, lead 20' may be connected to signal generator 1 through a lead extension 20. Extension 20 includes one or more contacts at the proximal and distal end portions that are electrically coupled through wires running through extension 20. Of course it will be understood that with some systems lead 20' may be directly connected to electrical signal generator 1 without use of a lead extension 20. It will be further understood that more than one lead 20' or lead extension 20 may be employed per signal generator 1.

While FIGS. 1 and 2 depict systems infusion devices and electrical signal generators, it will be understood that the teachings described herein may be applicable to virtually any known or future developed implantable medical device.

Referring to FIG. 3, alternative locations for implanting a medical device 1 are shown. As depicted in FIG. 3A, device 1 may be implanted in the pectoral region 7 of a patient. Alternatively, device 1 may be implanted in the head of a patient, more specifically behind the patient's ear (FIG. 3B), in the patient's abdomen (FIG. 3C) or in the patient's lower back or buttocks (FIG. 3D). Of course, device 1 may be placed in any medically acceptable location in patient.

Figure 4:
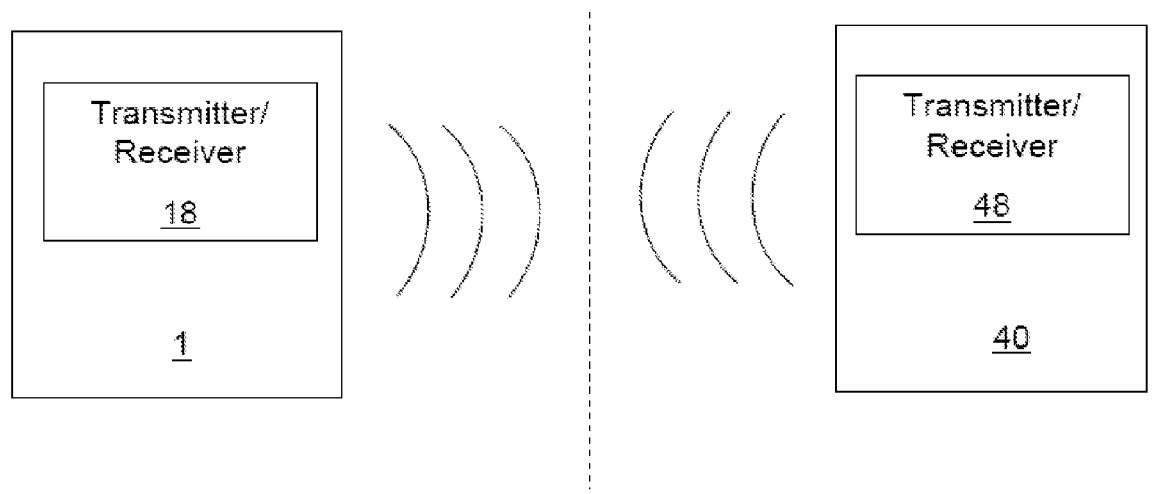
FIG. 4 is a diagrammatic representation of an external device in wireless communication with an implantable medical device.

Referring to FIG. 4, an external device 40 in wireless communication with implantable device 1 is shown. External device 40 may communicate with implantable device 1 through patient's skin, which is represented by the dashed line in FIG. 4. In various embodiments implantable device 1 carries out the various infection monitoring methods, or portions thereof, described herein. In some other embodiments the combination of implantable device 1 and external device 40 carry out the various infection monitoring methods, or portions thereof, described herein. In various embodiments, where implantable device 1 is a programmable device, external device 40 may be a programmer device, such as Medtronic Inc.'s N'Vision™ clinician programmer. Of course external device may be any device capable of wirelessly communicating with implantable device 1, such as a patient programmer, a computer, a personal data assistant, or the like. As shown in FIG. 4, implantable device 1 contains a wireless transmitter or receiver 18, and external device 40 contains a wireless transmitter or receiver 18 to allow implantable device 1 and external device 40 to communicate. External device 40 and implantable device 1 may be capable of one-way (external device 40 to implantable device 1 or implantable device 1 to external device 40) or two-way communication.

Figure 5A:
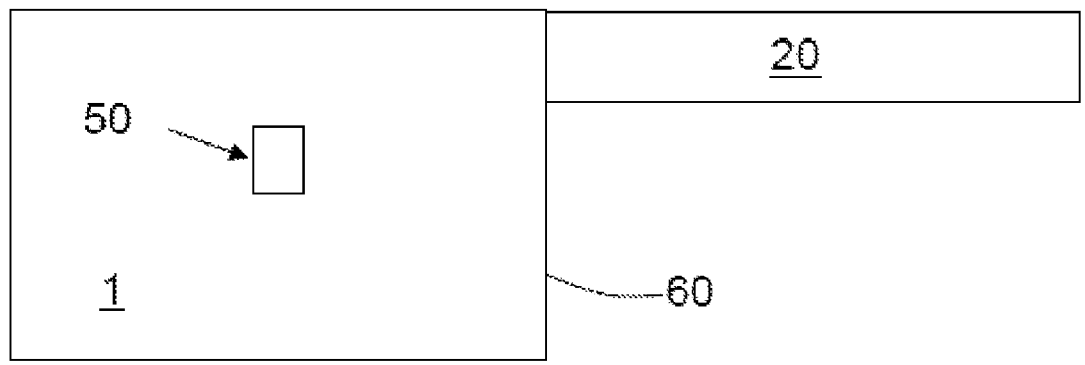
FIGS. 5A-B is a diagrammatic representation of a side view (5A) and back view (B) of an implantable medical device system having sensor(s) in proximity to the implantable device.
Figure 5B:
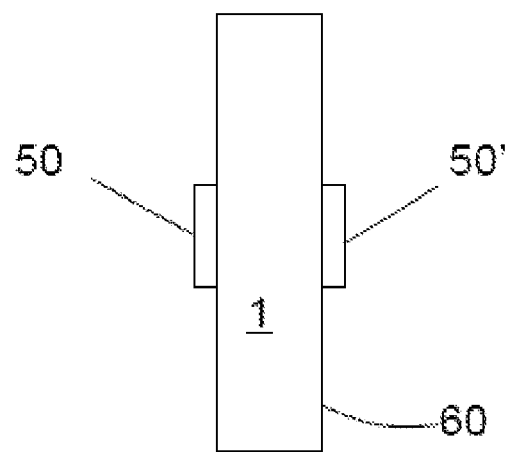

Referring to FIG. 5, sensor(s) 50, 50' associated with implantable active medical device 1 is shown. FIG. 5A is a side view of a representative active device 1 and associated device 20. FIG. 5B is a back view of a representative active device 1. One or more sensor 50, 50' may be located in proximity to device 1; e.g., disposed on, in, or near housing 60 of device 1. Sensor 50, 50' may be any device capable of detecting and transmitting information regarding an indicator of infection to device 1. If housing 60 is hermetically sealed, feedthroughs (not shown) may be used to provide electrical connectivity through housing 60 while maintaining the hermetic seal. While not shown, it will be understood that one or more sensor capable of detecting an indicator of infection may be located on, in, or about accessory device 20. Examples of physical or chemical stimuli that may serve as indicators of infection are temperature, impedance, pH, and biological markers of infection.

Changes in temperature in proximity to implanted device 1 may be used as an indicator of infection in proximity to device 1. The temperature of body tissue at a site of infection is generally greater than that of body tissue at a location removed from the site of infection. Accordingly, an increase in temperature in proximity to an implanted medical device 1 may serve as an indicator of infection. Any suitable sensor 50, 50' capable of detecting temperature or changes in temperature may be employed. For example, temperature sensor 50, 50' may include a thermocouple, a thermistor, a junction-based thermal sensor, a thermopile, a fiber optic detector, an acoustic temperature sensor, a quartz or other resonant temperature sensor, a thermo-mechanical temperature sensor, a thin film resistive element, or the like.

Changes in impedance of tissue in proximity to implanted device 1 may be used as an indicator of infection in proximity to device 1. For example, an increase in fluid in tissue is often observed at a site of an infection. Accordingly, a decrease in impedance of tissue in proximity may serve as an indicator of infection. In the case of impedance measurement, detection or monitoring, sensors 50, 50' are electrodes. Impedance may be measured between two electrodes. Current or voltage is applied between the electrodes with one electrode at any given time serving as a source and the other serving as a sink. In various embodiments, electrodes will be positioned at opposing surfaces of housing 60 of device 1. In other embodiments, one electrode may be located on accessory device 20, e.g. on a lead, and one may be located on housing of device 1. Alternatively, one electrode may be located on accessory device 20 and housing 60 of device 1 may serve as a return electrode, in a manner similar to unipolar signal generators. Further, it will be understood that more than one electrode pair may be employed to monitor impedance.

In instances where device 1 is an electrical signal generator, the electrical components used for generating therapeutic electrical signals may also be used for generating signals for impedance monitoring. In instances where device 1 is not an electrical signal generator, e.g. device 1 is an infusion pump, components capable of generating appropriate electrical signals for testing impedance of body tissue may be incorporated into device 1. Any impedance detection components or circuitry may be employed. For example, an ohm meter or a wheatstone bridge design may be used to measure or detect changes in impedance or resistance. Examples of additional suitable components or circuitry are described in, for example, the following patents and applications assigned to Medtronic, Inc.: US 2006/0259079; US 2006/0036186; US 2004/0162591; US 2003/0176807; U.S. Pat. Nos. 5,876,353; 5,824,029; and 5,282,840.

Changes in pH in proximity to implanted device 1 may be used as an indicator of infection in proximity to device 1. As pH may serve as a general indicator of the state of a tissue, a change in pH may be indicative of infection. Accordingly, a sudden or gradual change in pH in proximity to an implanted medical device 1 may serve as an indicator of infection. Any suitable sensor 50, 50' capable of detecting pH or changes in pH may be employed.

Any biological markers of infection may be detected in accordance with the teachings presented herein. Non-limiting examples of biological markers of infection include viral, fungal, or bacterial proteins or nucleic acids or fragments thereof. As most infections associated with implantable medical devices appear to be due to infection due to *Staphlococcus aureus*, *Staphlococcus epidermis*, *Pseudomonus auruginosa* and *Candidia* Sp., detection of proteins, nucleic acids, or fragments thereof of such microorganisms may be beneficial. Alternatively, detection of indicators of an immune response may be detected. For example, an increase in a pro-inflammatory cytokine. Non-limiting examples of proinflammatory cytokines include tumor necrosis factor (TNF; also known as TNFα or cachectin), interleukin (IL)-1α, IL-1β, IL-2; IL-5, IL-6, IL-8, IL-15, IL-18, interferon γ (IFN-γ); platelet-activating factor (PAF), thromboxane; soluble adhesion molecules; vasoactive neuropeptides; phospholipase A2; plasminogen activator inhibitor (PAI-1); free radical generation; neopterin; CD14; prostacyclin; neutrophil elastase; protein kinase; monocyte chemotactic proteins 1 and 2 (MCP-1, MCP-2); macrophage migration inhibitory factor (MIF), high mobility group box protein 1 (HMGB-1), and other known factors. Indication of an immune response may also be detected by an decrease in an anti-inflammatory cytokine in proximity to device 1. Non-limiting examples of anti-inflammatory cytokines include IL-4, IL-10, IL-17, IL-13, IL-1α, and TNFα receptor. It will be recognized that some of proinflammatory cytokines may act as anti-inflammatory cytokines in certain circumstances, and vice-versa. Such cytokines are typically referred to as plieotropic cytokines. An immune response may also be detected by measuring changes (baseline versus after device implant or other event, a first point after device implant or other event versus a second point after device implant or other event, etc.) in the presence of other factors involved in an immune response. Non-limiting examples of such other factors include TGF, PDGF, VEGF, EGF, FGF, I-CAM, and nitric oxide. In addition, an immune response may be detected by changes in chemokines, such as 6cKine and MIP3beta, and chemokine receptors, including CCR7 receptor. Further, an immune response may be measured by changes in immune cell population (upregulated Langerhans cells, dendritic cells, lymphocytes), or immune cell surface co-stimulatory molecules (Major Histocompatibility, CD80, CD86, CD28, CD40). An immune response may also be detected by measuring changes in other factors involved in the inflammatory cascade, for example in the signal transduction cascades including factors such as NFκ-B, Egr-1, Smads, toll-like receptors, and MAP kinases. In addition, an immune response may be detected by a change in the presence of an exogenous antigen believed to have caused an inflammatory response, such as, e.g., a bacteria, a virus, or a fungus.

Any sensor capable of detecting such biological markers indicative of infection may be used. In various embodiments, a biosensor is used to detect the presence of a molecule in proximity to implanted device 1. Any known or future developed biosensor may be used. The biosensor may have, e.g., an enzyme, an antibody, a receptor, or the like operably coupled to, e.g., a suitable physical transducer capable of converting the biological signal into an electrical signal. In some situations, receptors or enzymes that reversibly bind the molecule being detected may be preferred. In various embodiments, sensor 50, 50' includes an electrode with an ion selective coating that is capable of directly transducing the amount of a particular substance. An example of this type of transducer is described in the paper "Multichannel semiconductor-based electrodes for in vivo electrochemical and electrophysiological studies in rat CNS" by Craig G. van Horne, Spencer Bement, Barry J. Hoffer, and Greg A. Gerhardt, published in Neuroscience Letters, 120 (1990) 249-252. In various embodiments, sensor 50, 50' may be a sensor as described in, e.g., U.S. Pat. No. 5,978,702, entitled TECHNIQUES OF TREATING EPILEPSY BY BRAIN STIMULATION AND DRUG INFUSION or U.S. 2005/0209513, entitled COLLECTING SLEEP QUALITY INFORMATION VIA A MEDICAL DEVICE, filed Apr. 15, 2004, and published Sep. 22, 2005. Modifications of the teachings presented in the above-cited references may be made to account for one or more biological marker of infection.

For certain biological markers, e.g. proteins or nucleic acids or fragments thereof of microorganisms responsible for infection, merely the presence of such markers may be indicative of an infection. For other markers that may be present in a patient lacking an infection, e.g. cytokines and chemokines, increases or decreases in the levels of such markers may be indicative of an infection.

For the above-discussed indicators of infection or other indicator of infection, it may be desirable to compare levels of the indicators at a location in proximity to device 1 and at a location removed from device. Such comparisons may allow for a reduction in false positive detections. For example, elevation in temperature in proximity to device 1 may be due to localized infection or may be due to increased activity of the patient; increases in inflammatory cytokines in proximity to the device may be due to localized infection or a more general immune response; etc. By comparing the level of an indicator of infection in proximity to an implanted device to the level at a location removed from the device, a more accurate determination of whether an infection is present in proximity to the device may be made. Additional information regarding monitoring an indicator of infection at two locations is provided in U.S. patent application Ser. No. 11/737,171, entitled "Implantable Therapy Delivery System Having Multiple Temperature Sensors", filed on Apr. 19, 2007 and published on Oct. 23, 2008 as U.S. 2008/0262378, which application is hereby incorporated herein by reference in its entirety to the extent it does not conflict with the disclosure presented herein.

Information regarding a first indicator of infection may be used to determine whether an infection is present in proximity to the implanted device 1. In addition, one or more second indicators of infection may be used to determine whether the indication based on the first indicator is accurate. Additional information regarding infection monitoring using two or more indicators of infection is provided in U.S. patent application Ser. No. 11/737,181, entitled "Multi-Parameter Infection Monitoring", filed on Apr. 19, 2007, now U.S. Pat. No. 7,604,629, which application is hereby incorporated herein by reference in its entirety to the extent it does not conflict with the disclosure presented herein.

Figure 6:
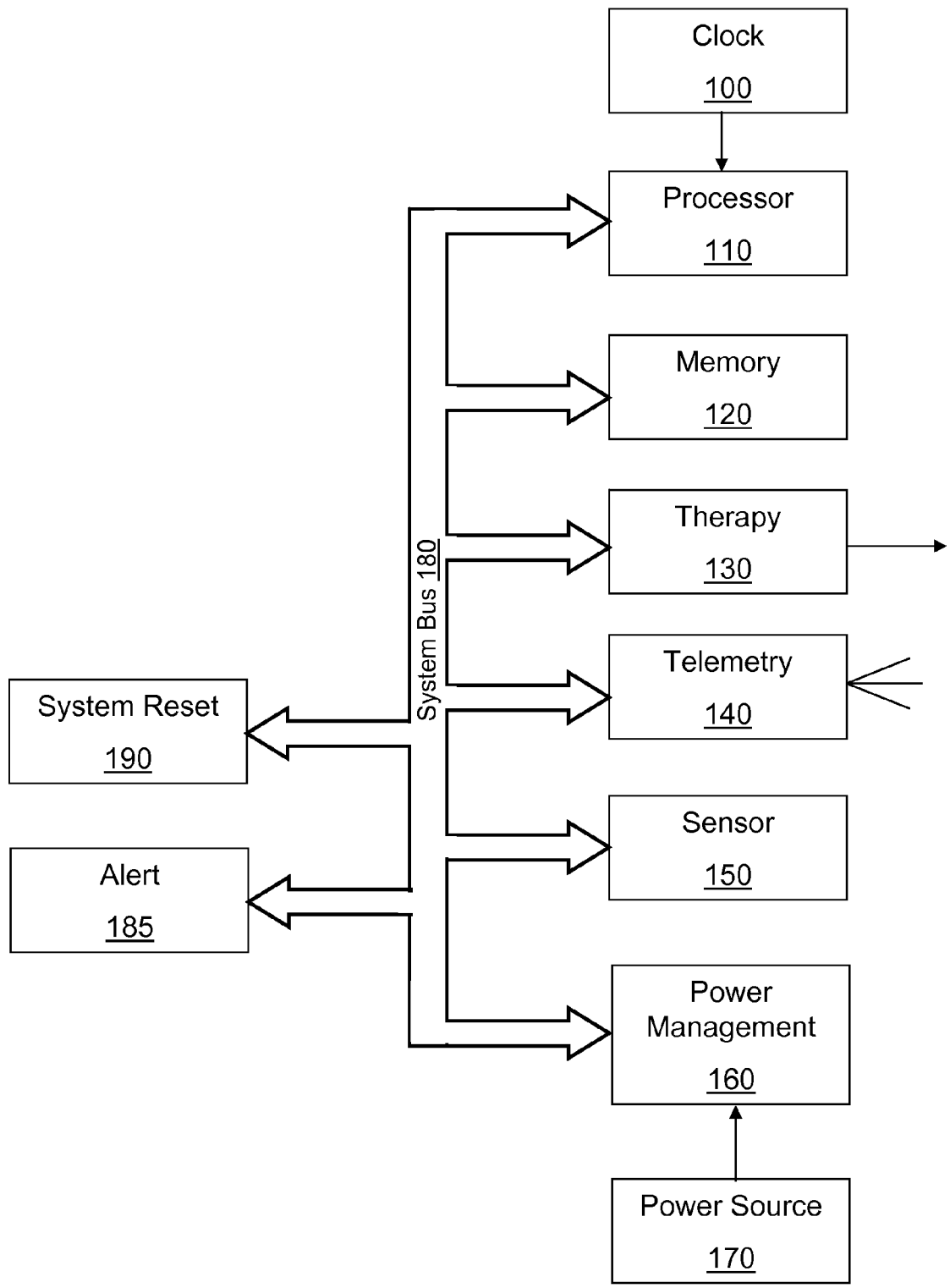
FIG. 6 is a schematic block diagram of representative components of an illustrative implantable medical device.

Referring to FIG. 6, some representative electronic components of an implantable medical device 1 according to various embodiments are shown in block form. Active implantable medical device 1 as depicted in the embodiment shown in FIG. 6 includes a clock 100, a processor 110, a memory 120, a therapy output or delivery component 130, a telemetry component 140, a sensor 150, a power management module 160, a power source 170, an alert module 185, and a system reset module 190. Other components of active implantable medical device 1 can include, e.g., a diagnostics module or recharge module (not shown). In an embodiment, all components except the power source 170 can be configured on one or more Application Specific Integrated Circuits (ASICs) or may be one or more discrete components, or a combination of both. Also, all components, except the clock and power source are connected to bi-directional data bus 180 that is non-multiplexed with separate address and data lines.

Processor 110 may be synchronous and typically operates on low power, such as Motorola 68HC11 synthesized core operating with a compatible instruction set. Clock 100 counts the number of seconds since a fixed date for date/time stamping of events and may be used for therapy control. Memory 120 includes memory sufficient for operation of device 1, such as volatile Random Access Memory (RAM) for example static RAM, nonvolatile Read Only Memory (ROM), Electrically Erasable Programmable Read Only Memory (EEPROM) for example Flash EEPROM, and register arrays configured on ASICs. Direct Memory Access (DMA) may be available to selected modules such as telemetry module 140 or sensor module 150, so that the selected modules can request control of data bus 180 and write data directly to memory 120 bypassing processor 110. System Reset 190 controls operation of ASICs and modules during power-up of device 1, so ASICs and modules registers can be loaded and brought on-line in a stable condition.

Telemetry 140 module or other wireless module provides for communication between implantable device 1 and external device 40 such as a programmer. Communication may be bi-directional. Telemetry module 140 generally includes a telemetry antenna, a receiver 18 (see, e.g., FIG. 4), a transmitter 48 (see, e.g., FIG. 4), and a telemetry processor. Telemetry modules are generally known in the art and are further detailed in U.S. Pat. No. 5,752,977, entitled "Efficient High Data Rate Telemetry Format For Implanted Medical Device" issued to Grevious et al. (May 19, 1998). While module 140 is referred to herein as "telemetry" module, it will be understood that other forms of wireless communication may readily be substituted where appropriate for telemetry. Examples of forms of wireless communication include Bluetooth®, 802.11, and Medical Implant Communication Service (MICS) frequency band communication.

Therapy module 130 refers to components for carrying out the delivery or generation of therapeutic output to be delivered to a patient from active device 1. One of skill in the art will appreciate that the components may vary on a device-by-device basis and a therapy-by-therapy basis. For example, therapy module 130 may contain an oscillator if device 1 is an electrical signal generator and may contain a pumping mechanism if device 1 is an infusion device.

Sensor module 150 includes circuitry associated with one or more sensors 50, 50' and may include other components for transmitting sensed information from sensor 50, 50' to, e.g., processor 110 or memory 120. Sensor module 150 or other components of device 1 may include one or more analog to digital converters to convert analog signals generated by sensor 50 into digital signals usable by processor 110, as well as suitable filter and amplifier circuitry.

Alert module 185 may issue an alert, e.g. an audible alert or tactile alert, such as a vibration. An alert may be issued if information indicative of an infection is detected. The alert will serve to prompt the patient to seek medical attention.

While not shown, device 1 may be rechargeable and include a recharge module. Additional information regarding rechargeable implantable medical devices and infection monitoring is provided in U.S. patent application Ser. No. 11/737,179, entitled "CONTROLLING TEMPERATURE DURING RECHARGE FOR TREATMENT OF CONDITION", filed on Apr. 19, 2007 and published on Jan. 1, 2009 as U.S. 2009/0005770, which application is hereby incorporated herein by reference in its entirety to the extent that it does not conflict with the disclosure presented herein.

It will be understood that the components described in FIGS. 1-6 are but examples of components that an implantable device 1 may have and that many other device or system configurations may be employed to carry out the methods described below. However, for the sake of convenience, the discussion that follows with regard to the method illustrated in the flow diagrams of FIGS. 7 and 8 will refer to components as described with regard to FIGS. 1-6.

Figure 7:
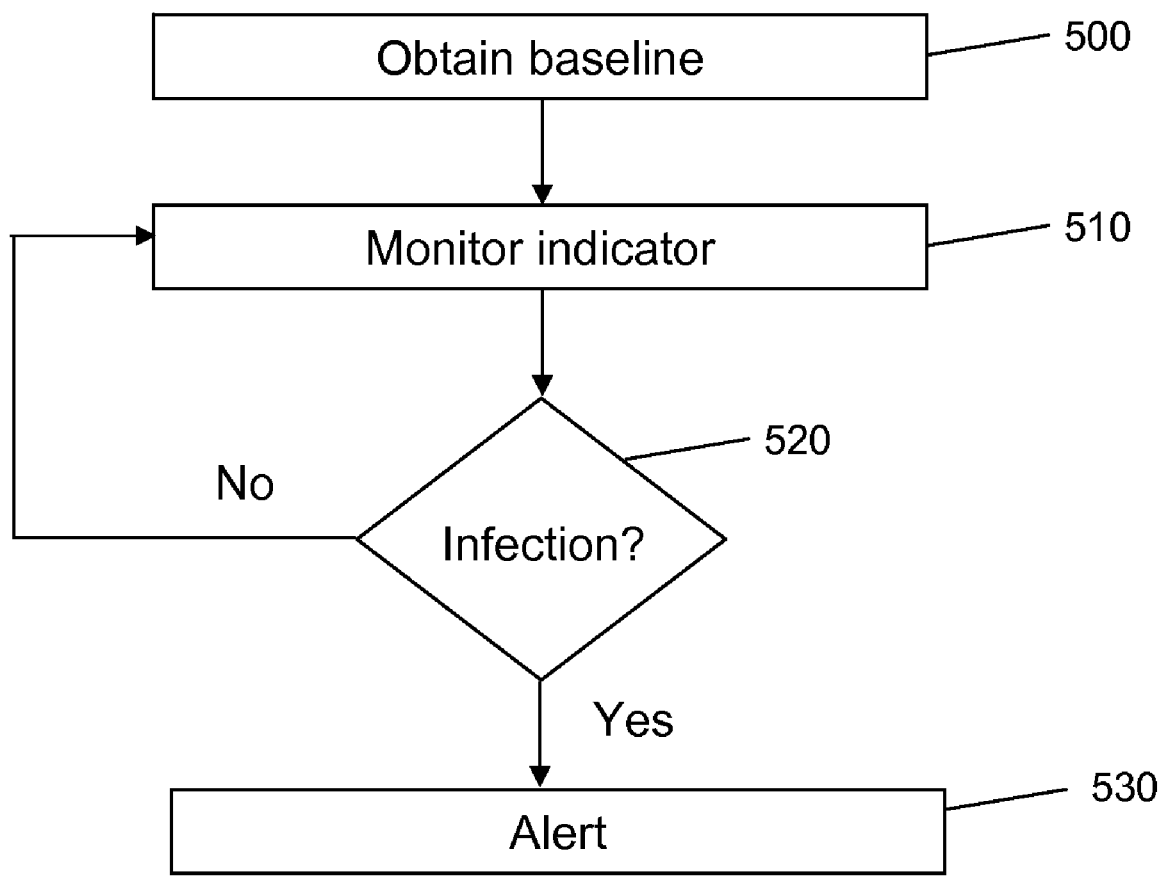
FIGS. 7 and 8 are flow diagrams of representative methods.

In the embodiment depicted in FIG. 7, a baseline value for an indicator of infection is obtained (500). In various embodiments, the baseline value may be obtained by a sensor 50, 50' and stored in memory 120. In addition, an indicator of infection in proximity to the device is monitored (510). As with the baseline value, a sensor 50, 50' may detect a monitored indicator of infection. Sensor 50, 50' may send a signal regarding the indicator to memory 120 via sensor module 150. A determination is then made as to whether the monitored indicator is indicative of infection (520). The determination (520) includes comparing a value associated with the monitored indicator to the baseline value. For example, processor 110 may compare a baseline value retrieved from memory 120 to a monitored value retrieved from memory 120 to determine whether the indicator is indicative of infection. If a determination is made that the monitored indicator is indicative of infection, an alert may be issued (530). If the monitored indicator is not indicative of infection, the indicator may continue to be monitored (510).

The baseline value may be obtained at any suitable time, such as when conditions are stable. Conditions may be determined to be stable in a variety of ways. For example, if signals associated with a sensed indicator of infection do not vary beyond a predetermined amount over a predetermined period of time, conditions with regard to the indicator may be considered stable and a baseline value may be obtained. Often, acceptable variation, and thus stability, can be based on a percentage of a value of a sensed signal. For example, a variation of less than 10%, less than 5%, or less than 1% over a predetermined period of time may be considered stable. Of course, variation of less than a predetermined absolute value may also be used to determine stability. It will be understood that acceptable variation will be dependent on the indicator being sensed. For example, a change in temperature of less than 1° F. (e.g., a 2° F. range of ±1° F.) over 24 hours may be considered stable, or a change in pH of less than 0.1 (e.g., a 0.2 range of ±0.1) over 24 hours may be considered stable.

A baseline value may be obtained at a time deemed appropriate by a physician or other health care provider. For example, a physician may determine that a patient is free from infection in proximity to the implanted device 1 and may instruct the implanted device 1 via an external device 40, such as a physician programmer, to obtain a baseline value regarding an indicator of infection via sensor 50, 50'. The baseline value may be obtained immediately upon receipt of instruction from external device 40, following a determination of stable conditions (e.g., as discussed above) following receipt of instruction from external device 40, following a predetermined time from receipt of instruction from external device 40, or the like.

A baseline value may be obtained a predetermined time following implantation of a device. Depending on the indicator of infection, it may be advantageous to wait until conditions within the patient have stabilized prior to obtaining the baseline value. For example, surgical implantation of the device 1 and any associated device 20 typically results in increased fluid in the tissue in proximity to the device 1, in increased inflammatory cytokines in proximity to the device 1, and in increased localized tissue temperature in proximity to the device 1. Thus, incorrect determinations as to whether an infection is present in proximity to the implanted device 1 may result if the determination is based on impedance (influenced by fluid), levels of certain biological indicators of infection (e.g., cytokines), or temperature. The amount of time for conditions to stabilize will vary based on the indicator being detected. However, the amount of time before obtaining a baseline value should be balanced against the amount of time before an infection develops, which typically is within a few weeks following implantation.

In various embodiments it is desirable to monitor infection before the passage of the predetermined amount of time following implantation. While it may be difficult to obtain a stable baseline value before the passage of the predetermined amount of time, it is possible to determine whether an infection is likely to be present in proximity to the implanted device 1 prior to the predetermined time. For example, an increase in temperature in proximity to the device may be expected following implant. However, an increase greater than a predetermined amount, e.g. 3° F., or a temperature over 101° F. may be indicative of infection despite some of the increase in temperature being due to trauma associated with the surgical implantation of the device 1 rather than infection. Accordingly, even in situations where a stable baseline may not be readily obtainable, it may be desirable for infection monitoring to occur.

In various embodiments, an initial baseline value is obtained and additional baseline values of an indicator of infection are obtained with the passage of time. For example, a baseline value may be obtained every hour, day, week, or month. The baseline value may be obtained at a prescribed time or once stable conditions with regard to the indicator have been achieved at the prescribed time. Such embodiments may be beneficial in circumstances where the sensor signal may drift or degrade. For example, a signal received from a sensor 50, 50' for a given stimulus may change over time. Such a change might result in a false determination as to infection status when compared to a baseline obtained at or near implantation. Such false determinations are less likely to occur if the value is compared to a baseline value obtained closer in time.

In various embodiments, baseline values may be rejected if they fall outside a predetermined acceptable range. For example, a sensed temperature of 100° F. may be rejected as an acceptable baseline value. Yet, due to patient-to-patient variability it may be appropriate to allow such rejections to be overridden. For example, if a physician determines that no infection is present in proximity to the device 1 despite a sensed temperature of 100° F., a physician may instruct device 1, via an external device 40, to accept the sensed temperature as the baseline.

It will be understood that a baseline value can be a mean, median, or the like. It will be further understood that a baseline value may be a value associated with more than one indicator of infection.

Determinations as to whether a monitored indicator is indicative of infection that take into account a baseline can be more accurate. Such determinations are generally made by determining whether changes or trends relative to the baseline are indicative of infection, as opposed to absolute values of the monitored indicators. As discussed above a temperature of 100° F. may be an infection-free baseline value for one patient and may be a value indicative of infection in another patient or may be indicative of infection within a patient at one point in time but not at another time. However, an increase in temperature of 3° F. from baseline may be indicative of infection in both patients.

Suitable changes or trends in values associated with indicators of infection relative to baseline that are indicative of infection may be stored in look-up tables in memory 120. Processor 110 may compare values associated with monitored indicators to baseline values to determine whether the compared values are within such stored ranges to determine whether an infection is likely to be present in proximity to the implanted device 1. Those skilled in the art will be able to readily determine what changes or trends warrant a determination of infection with regard to one or more indicator of infection. For example, an increase in temperature of 4° F. from baseline, an increase in temperature of 3° F. from baseline for three hours or more, or an increase in temperature of 2.5° F. from baseline for twelve hours or more may be considered to be indicative of infection. By way of further example, a change in pH of 0.3 relative to baseline or a 10% change in impedance relative to baseline may be considered indicative of infection. Additional information regarding parameters and trends that may be indicative of infection are described in U.S. patent application Ser. No. 11/737,180, entitled "Indicator Metrics for Infection Monitoring", filed on Apr. 19, 2007, now U.S. Pat. No. 7,611,483, which is incorporated herein by reference in its entirety to the extent that it does not conflict with the disclosure presented herein; and (ii) U.S. patent application Ser. No. 11/737,181, entitled "Multi-Parameter Infection Monitoring" filed on Apr. 19, 2007, now U.S. Pat. No. 7,604,629.

Figure 8:
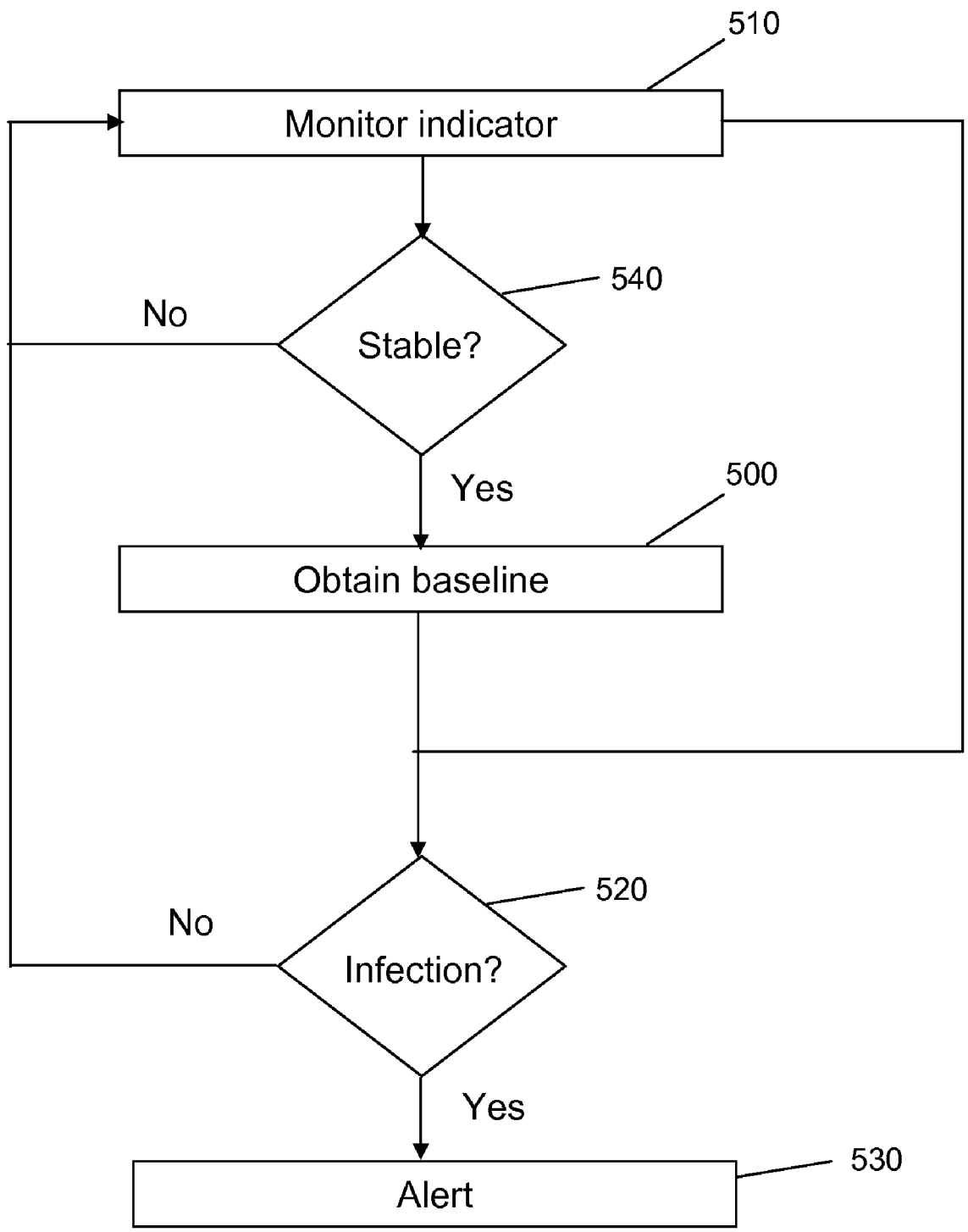

Referring to FIG. 8, a flow diagram of an illustrative method is shown. The method includes monitoring an indicator of infection in proximity to the implanted device 1 (510) and determining whether the monitored indicator is stable (540), e.g. as discussed above. By way of example, processor 110 may compare monitored indicator value obtained over time to predetermined acceptable ranges of stability stored in memory 120 to determine whether the monitored indicator is stable. If the monitored indicator is determined to be stable, a baseline may be obtained (500). Following obtaining a baseline, a determination as to whether a monitored indicator is indicative of infection, in comparing to baseline, may be made (520).

Figure 9A:
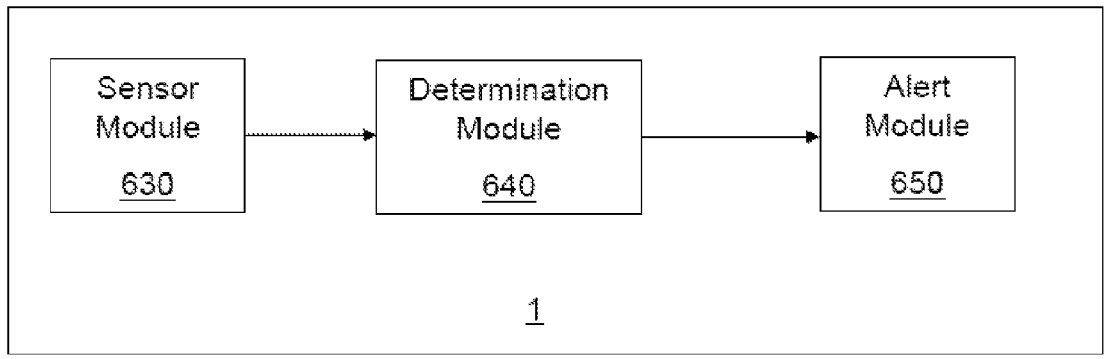
FIGS. 9A-C are schematic block diagrams of a representative implantable medical devices or systems.
Figure 9B:
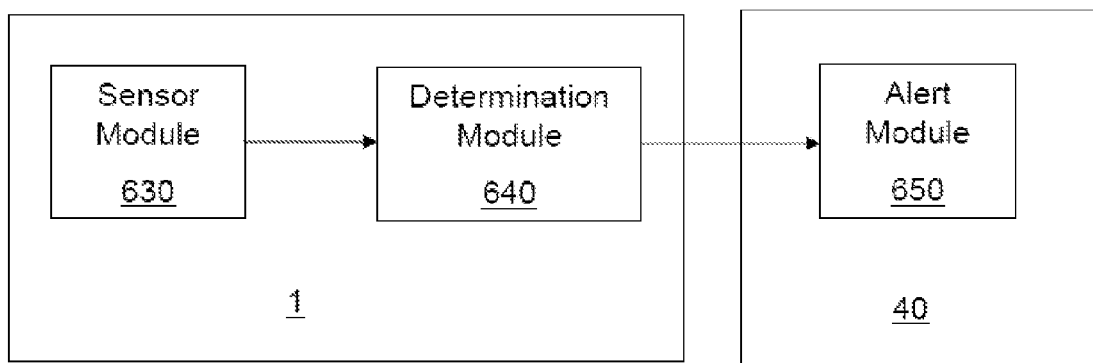
Figure 9C:
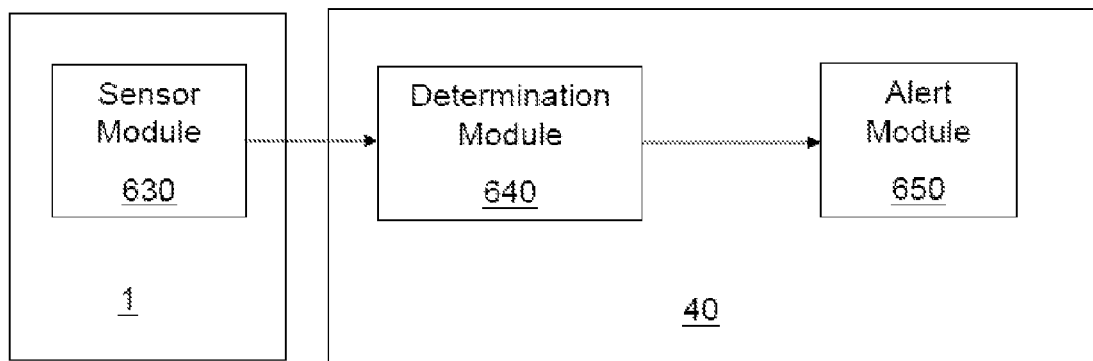

FIGS. 9A-C are block diagrams of representative devices or systems. It will be understood that one or more components described with regard to FIGS. 1-6 may be included or carry out a function of one or more modules described in FIGS. 9A-C. As shown in FIGS. 9A-C, a system or device suitable for carrying out methods as discussed with regard to FIGS. 7 and 8 may include a sensor module 630, a determination module 640, and an alert module 650. Determination module 640 may make a determination as to whether information from sensor module 630 is indicative of an infection (520). If the sensed information is indicative of infection, alert module 650 may provide an alert (530). As shown in FIG. 9A, all of the components may be included within an implantable medical device 1. Alternatively, some of the components may be included in an external device 40 as shown in FIGS. 9B-C. Thus, as shown in FIG. 9B, alert module 650 may be included in an external device 40. In the embodiment shown in FIG. 9C, determination module 640 and alert module 650 may be included in an external device 40. Of course, a variety of other distributions of modules between an implantable medical device and an external device are possible.

One of skill in the art will understand that components or steps described herein regarding a given embodiment or set of embodiments may readily be omitted, substituted, or added from, with, or to components or steps of other embodiments or sets of embodiments, as appropriate or desirable.

It will be further understood that a computer readable medium containing instructions that when implemented cause an implantable medical device (or system including an implantable medical device) to perform the methods described herein are contemplated. In an embodiment the computer readable medium contains instructions that when implemented cause an implantable medical device to (i) obtain a baseline value for an indicator of infection in proximity to the device; (ii) monitor the indicator of infection in proximity to the device; and (iii) determine whether the monitored indicator is indicative of infection in proximity to the device. The determination includes comparing a value associated with the monitored indicator to the baseline value. Devices including the computer readable medium are also contemplated.

Patent applications that may provide additional insight into the teachings provided herein include the following: (i) U.S. patent application Ser. No. 11/737,173, entitled "Infection Monitoring", filed on Apr. 19, 2007 and published on Oct. 23, 2008 as U.S. 2008/0262332; (ii) U.S. patent application Ser. No. 11/737,170, entitled "Infection Monitoring", filed on Apr. 19, 2007 and published on Oct. 23, 2008 as U.S. 2008/0262331; (iii) U.S. patent application Ser. No. 11/737,176, entitled "Refined Infection Monitoring", filed on Apr. 19, 2007, now U.S. Pat. No. 7,682,355; (iv) U.S. patent application Ser. No. 11/737,169, entitled "Event Triggered Infection Monitoring", filed on Apr. 19, 2007 and published on Oct. 23, 2008 as U.S. 2008/0262374; and (v) U.S. Provisional Application Ser. No. 60/912,078, entitled "Heating Implantable Device to Treat a Condition", filed on Apr. 19, 2007. Each of the above-referenced patent applications is hereby incorporated herein by reference in their respective entireties to the extent that they do not conflict with the disclosure presented herein.

Thus, embodiments of BASELINE ACQUISITION FOR INFECTION MONITORING are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A method performed by an implantable medical device, comprising:
   obtaining via a sensor an initial baseline value for an indicator of infection in proximity to the implantable medical device; monitoring the indicator of infection in proximity to the device via the sensor; and determining whether the monitored indicator is indicative of infection, wherein determining whether the monitored indicator is indicative of infection comprises comparing a value associated with the monitored indicator to the initial baseline value;
   receiving instructions from an external device to obtain an additional baseline value for an indicator of infection in proximity to the implantable medical device; and
   obtaining the additional baseline value via the sensor operably coupled to the device following receipt of the instructions; monitoring the indicator of infection in proximity to the device via the sensor; and determining whether the monitored indicator is indicative of infection in proximity to the device, wherein determining whether the monitored indicator is indicative of infection comprises comparing a value associated with the monitored indicator to the additional baseline value.

2. The method of claim 1, wherein the instructions received from the external device instruct the implantable device to obtain the additional baseline value at a predetermined time following implantation of the device.

3. The method of claim 1, wherein the indicator of infection is temperature.

4. The method of claim 1, further comprising providing an alert if the monitored indicator is determined to be indicative of infection.

5. A non-transitory computer readable medium containing instructions that when implemented cause an implantable medical device to:
   obtain via a sensor an initial baseline value for an indicator of infection in proximity to the implantable medical device; monitor the indicator of infection in proximity to the device via the sensor; and determine whether the monitored indicator is indicative of infection, wherein the determination comprises comparing a value associated with the monitored indicator to the initial baseline value;
   receive instructions from an external device to obtain an additional baseline value for an indicator of infection in proximity to the implantable medical device; and
   obtain the additional baseline value via the sensor for an indicator of infection in proximity to the device; monitor the indicator of infection in proximity to the device; and determine whether the monitored indicator is indicative of infection in proximity to the device, wherein the determination comprises comparing a value associated with the monitored indicator to the additional baseline value.

6. An implantable medical device comprising:
   a sensor capable of detecting an indicator of infection;
   electronics operably coupled to the sensor and configured to monitor an infection in proximity to the device; and
   a computer readable medium according to claim 5 readable and executable by the electronics.

7. A method performed by an implantable medical device, comprising:
   monitoring an indicator of infection in proximity to the device via a sensor of an implantable medical device;
   obtaining via the sensor an initial baseline value for the indicator of infection in proximity to the implantable medical device; and determining whether the monitored indicator is indicative of infection, wherein determining whether the monitored indicator is indicative of infection comprises comparing a value associated with the monitored indicator to the initial baseline value;
   determining whether a value associated with the monitored indicator is stable and setting the stable value as an additional baseline; and
   determining whether the monitored indicator is indicative of infection in proximity to the device, wherein determining whether the monitored indicator is indicative of infection comprises comparing a value associated with the monitored indicator to the additional baseline value.

8. The method of claim 7, wherein the indicator of infection is temperature and determining whether a value associated with the monitored indicator is stable comprises determining whether the temperature has varied less than $\pm 1°$ F. over 24 hours.

9. The method of claim 7, wherein determining whether a value associated with the monitored indicator is stable occurs at a predetermined time following implantation of the implantable device.

10. The method of claim 7, further comprising receiving instructions from an external device to determine whether the value associated with the monitored indicator is stable.

11. The method of claim 7, further comprising providing an alert if the monitored indicator is determined to be indicative of infection.

12. A non-transitory computer readable medium containing instructions that when implemented cause an implantable medical device to carry out the method of claim 7.

13. An implantable medical device comprising:
   a sensor capable of detecting an indicator of infection;
   electronics operably coupled to the sensor and configured to monitor an infection in proximity to the device; and
   a non-transitory computer readable medium according to claim 12 readable and executable by the electronics.

* * * * *